United States Patent [19]

Feinstein et al.

[11] 4,177,219
[45] Dec. 4, 1979

[54] PROCESS FOR SELECTIVE ETHYL SCISSION OF ETHYLAROMATICS TO METHYLAROMATICS

[75] Inventors: Allen I. Feinstein, Wheaton, Ill.; Ralph J. Bertolacini, Chesterton, Ind.; Dae K. Kim, Naperville, Ill.

[73] Assignee: Standard Oil Company (Indiana), Chicago, Ill.

[21] Appl. No.: 899,314

[22] Filed: Apr. 24, 1978

[51] Int. Cl.$^2$ .............................................. C07C 3/58
[52] U.S. Cl. ...................................... 585/489; 208/46
[58] Field of Search ................................... 260/672 R

[56] References Cited

U.S. PATENT DOCUMENTS

| 2,422,673 | 6/1947 | Haensel et al. | 260/672 R |
| 3,306,944 | 2/1967 | Pollitzer | 252/466 PT |
| 3,992,468 | 11/1976 | Cosyns et al. | 260/672 R |

Primary Examiner—Veronica O'Keefe
Attorney, Agent, or Firm—William C. Clarke; Arthur G. Gilkes; William T. McClain

[57] ABSTRACT

Ethyl aromatics contained in the $C_9$ aromatic fraction from fractionated reformate are selectively converted to xylenes via ethyl scission in the presence of a catalyst comprising a carrier of highly purified gamma alumina containing essentially no silica and of a surface area of at least 100 m$^2$/g and a metal selected from the group consisting of a Group VIII metal and a Group VIII metal promoted with zinc.

15 Claims, No Drawings

PROCESS FOR SELECTIVE ETHYL SCISSION OF ETHYLAROMATICS TO METHYLAROMATICS

BACKGROUND OF THE INVENTION

This invention relates to a method for the selective scission of the carbon-to-carbon bond of the ethyl group of ethyl aromatics to produce methyl aromatics. Alkyl aromatic compounds have long been produced from hydrocarbon fractions relatively rich in such materials. Early sources were liquids from coking or other distillation of coals. More recently, these products have been derived from fractions obtained in refining of petroleum. An important source in recent years has been the aromatic liquid naphthas resulting from the thermal cracking of gases and naphthas to produce olefins.

However derived, these aromatic-rich streams containing a broad range of components have usually been distilled and otherwise separated (e.g. solvent extraction) to obtain the desired product components. The purpose of those operations typically has been to obtain paraxylene and benzene which are now used in huge quantities in the manufacture of terephthalic acid and other chemical products. The separated streams resulting from the above separation by distillation or other means accordingly consist of product streams of benzene, toluene, $C_8$ aromatics containing xylenes and a bottoms product of $C_9$ aromatics containing ethyltoluenes, trimethylbenzenes and $C_{10}+$ aromatics. The $C_9$ component can be separated by means of distillation and can be a source material for manufacture of lighter aromatic hydrocarbons by hydrocracking but with some attendant material losses. The $C_{10}$ component is useful for heavy solvents and gasoline.

The transalkylation of toluene and $C_9$ aromatics including trimethylbenzenes has been widely studied (U.S. Pat. Nos. 3,260,764; 3,527,825; 3,677,973) because of the demand for greater quantities of high purity aromatic hydrocarbons but the results of such studies have not been sufficient to cause supplies of these hydrocarbons to increase sufficiently to meet this demand. One of the sources of $C_9$ aromatics can be the heavy reformate stream obtained in refining of petroleum; however, the trimethylbenzene concentration in heavy-reformate derived $C_9$ aromatics often is only 50–60%. The remaining $C_9$ aromatics content can consist of 35–42% ethyltoluenes and 6–10% propylbenzenes and indan. The presence of ethyltoluenes and propylbenzenes in a transalkylation reaction feed can have a detrimental effect on both xylene yield and quality, because they can contribute to the formation of undesirable by-products such as ethylxylenes and ethylbenzenes. Accordingly, it is advantageous to remove the ethyltoluenes from reformate-derived $C_9$ aromatics, preferably by converting them to useful compounds such as xylenes. This would provide also a trimethylbenzene-rich stream which is ideally suitable as transalkylation feedstock.

This invention relates to an ethyl scission process for the selective conversion of fractionated heavy reformate comprising ethyltoluenes into more useful compounds. More specifically, this invention is concerned with a selective scission process whereby a fractionated heavy reformate stream comprising ethyltoluenes is converted primarily to xylenes while formation of benzene is minimized, utilizing a catalyst comprising a metal selected from Group VIII metals and Group VIII metals promoted with zinc on a carrier of highly purified gamma alumina containing essentially no silica and of a surface area of at least 100 $m^2/g$. Fractionated heavy reformates are reformates from which $C_8$ aromatics and lighter components have been largely removed. This stream typically contains $C_9$ aromatics consisting primarily of trimethylbenzenes and ethyltoluenes in a respective ratio of approximately 1.8:1. Ethyl scission of the ethyltoluenes contained in this fraction to xylenes can provide a trimethylbenzene-rich $C_9$ aromatic stream which is ideally suited for preparing additional xylenes via transalkylation with toluene.

In the prior art, methods, which have been used to produce aromatic chemicals from fractionated heavy reformates, can utilize a hydrocracking and/or a hydrodealkylation step to convert the $C_9$ and $C_{10}+$ aromatic components to benzene, toluene and $C_8$ aromatics. The $C_6+$ paraffins are converted into readily distillable low boiling hydrocarbons of $C_5$ and lighter. Processes utilizing these principles are described in U.S. Pat. Nos. 3,957,621 and 3,862,254.

Extensive experiments in the prior art on hydrodealkylation of pure methylethyl and trimethylbenzenes and of mixed alkylbenzene feeds obtained from heavy reformate in the presence of certain catalysts have demonstrated the effects of the nature of the feed and catalyst in the yields and ratios of the xylene isomers produced. For example, alkalized cobalt molybdate catalyst favored p-xylene whereas nickel catalyst produced high percentages of o-xylene with extensive hydrogenolysis of the aromatic ring. *Riv. Combust.* 20 No. 1:3–35 (Jan 1966).

Other typical prior art on hydrodealkylation of alkyl aromatics is the following:

U.S. Pat. No. 2,422,673 teaches hydrodealkylation or demethylation of an alkyl aromatic using a catalyst containing nickel or cobalt on diatomaceous earth. Temperatures used in the process are between 350–650° F. and pressures are between subatmospheric to 1000 psig. The reaction is carried out at a low pressure of hydrogen so as to obtain a high proportion of demethylation and a relatively small amount of hydrogenation of aromatic hydrocarbons to naphthenic hydrocarbons.

U.S. Pat. No. 2,734,929 teaches hydrodealkylation of alkyl aromatics. Ethylbenzene is hydrocracked to principally benzene and xylene to toluene. The catalyst contains a Group VIB or Group VIII metal hydrogenation component such as chromium, molybdenum, tungsten, iron, cobalt, ruthenium, rhodium, etc. The catalyst is preferably suspended on a carrier which has no adverse effect on the reaction. Gel alumina, which contains silica and which usually has a surface area of over 100 $m^2/g$, as measured by gas adsorption, is preferred. The process requires a gaseous diluent which, column 2, lines 16–18, is stated as being a critical feature of the invention. Operating conditions include a temperature between 800°–1500° F. and a pressure of 0–5000 psig.

U.S. Pat. No. 3,478,120 discloses a process for hydrodealkylation of ethylbenzene to toluene, benzene, methane and ethane with the hydrodealkylation being carried out in the presence of xylenes. The catalyst used comprises an iron group metal on calcium aluminate. Operating conditions include a temperature range of 500°–1200° F. and pressure from atmospheric to 2000 psig.

U.S. Pat. No. 3,306,944 teaches a catalytic hydrodealkylation of alkyl aromatic hydrocarbons. Examples are cumene to ethylbenzene, predominantly, and toluene;

p-t-butyltoluene to p-propyltoluene, p-ethyltoluene and xylene. The catalyst comprises a metal selected from the group consisting of rhodium, ruthenium, etc. upon a promoted metal oxide support. "Promoted" refers to a pretreatment of the support with a salt or hydroxide of an alkali metal or alkaline earth metal. The preferred metal oxide support is gamma alumina which has a surface area ranging from 100 to about 300 m$^2$/g and is freed from combined or adsorbed water.

U.S. Pat. No. 3,992,468 teaches a catalytic hydrodealkation process of alkyl aromatic hydrocarbons to benzene. The catalyst comprises at least two metals, one selected from the group consisting of ruthenium, cobalt, osmium, palladium, rhodium, iridium, platinum, chromium, molybdenum, tungsten and manganese, the other selected from, among others, zinc, cadmium, and gallium, the final catalyst having a specific surface area of from 1 to 100 m$^2$/g. The carrier is of low acidity and can be alumina, including gamma alumina, magnesia, magnesia-silica, acidic alumina, alumina-silica, among others, including molecular sieves.

U.S. Pat. No. 3,975,454 teaches a catalytic hydrodealkylation process of alkyl aromatic hydrocarbons at a temperature within the range of 250°–400° C. The catalyst comprises the compounds formed from either graphite and an alkali metal, or graphite, an alkali metal and a compound of a metal selected from the group consisting of Group VIII of the Periodic Table which includes iron, nickel, cobalt, etc. Surface area of the catalyst of Example I was cited as about 20 m$^2$/g.

Accordingly, the prior art teaches catalytic hydrocracking and/or hydrodealkylation of alkyl aromatic hydrocarbons. However, the catalytic ethyl scission of alkyl aromatic hydrocarbons is not taught wherein the hydrocarbon comprises ethyltoluenes and the catalyst used comprises a metal selected from the group consisting of a Group VIII metal and a Group VIII metal promoted with zinc upon a high-surface area carrier of highly purified gamma alumina containing essentially no silica, with a surface area greater than 100 m$^2$/g under process conditions which selectively convert ethyltoluenes to predominantly xylenes.

SUMMARY OF THE INVENTION

A highly selective ethyl scission process for selectively demethylating ethyl aromatics to methyl aromatics which process comprises contacting an alkyl aromatic feedstock with hydrogen in the presence of a catalyst comprising a metal selected from the group consisting of a Group VIII metal and a Group VIII metal promoted with zinc on a high surface area carrier of highly purified gamma alumina containing essentially no silica with a surface area of at least 100 m$^2$/g at a temperature in the range from about 600° to 1000° F. and a pressure of from about 100 to 500 psig.

DETAILED DESCRIPTION OF THE INVENTION

The process of this invention is a process for the selective scission of ethyl groups of aromatic petroleum hydrocarbons. Particularly, it is a process for the selective demethylation of ethyl aromatic hydrocarbons wherein the carbon-to-carbon bond of the ethyl group is cleaved. When the process is applied to a C$_9$-rich aromatic reformate feed, among the resulting products is a trimethylbenzene-rich stream which is typically a desirable feed for a transalkylation unit.

The success of this scission process is due primarily to the use of particular catalytic compositions which are employed therein and the operating conditions that are used.

Typical feedstocks of the present invention are petroleum hydrocarbon streams which contain single-ring aromatic hydrocarbons which boil above about 275° F. and contain 8–10 carbon atoms. Such aromatic hydrocarbon streams can be a petroleum hydrocarbon fraction derived from petroleum reformate and which is known as heavy reformate. For purposes of this invention, the term "heavy reformate" is defined as the heavy fraction obtained from a catalytic reformer with a boiling point range of 275° F. to 430° F. comprising C$_8$–C$_9$ aromatics, C$_{10}$ aromatics and heavier components. Fractionated heavy reformate is defined as that fraction of heavy reformate from which the C$_{10}$'s and heavier components have been largely removed, leaving typically a C$_9$-rich aromatic stream. Accordingly the feedstock of this invention can contain ethyltoluene, propylbenzenes, trimethylbenzenes and indan.

Typically the feedstock is mixed with a hydrogen-containing gas and preheated to a suitable temperature, and then transferred to the reaction zone, which may contain one or more reactors. Advantageously, the feed is substantially completely vaporized before being introduced into the reaction zone.

The feedstock is contacted in the reaction zone with the hereinafter described catalyst in the presence of hydrogen or a hydrogen-affording gas. Advantageously, a hydrogen-to-hydrocarbon mole ratio of at least 4:1 is employed, and the hydrogen-to-hydrocarbon mole ratio can range from 1:1 up to 20:1. Preferably, the hydrogen-to-hydrocarbon mole ratio can range between 5:1 to about 9:1 at pressures of 150 to 250 psig respectively. Contact time can range from 1 to 20 seconds, preferably 3 to 10 seconds. Contact time is defined as bulk volume of the catalyst divided by volumetric flow rate of reactants and hydrogen. Other operating conditions comprise an elevated temperature of about 600° F. to about 1000° F., preferably about 800° F. to about 900° F.; an elevated pressure of about 100 psig to about 500 psig, preferably about 170 psig to about 250 psig; and about 0.01 to about 20 weights of hydrocarbon per hour per weight of catalyst (WHSV), preferably about 1 to about 10 weights of hydrocarbon per hour per weight of catalyst.

The catalytic composition of the process of this invention comprises a scission component disposed on an inorganic oxide support. The scission component comprises one member selected from the group consisting of the metal or oxide of metals of Group VIII of the Periodic Table of Elements and mixtures thereof. The pertinent Periodic Table of Elements may be found on the inside of the back cover of HANDBOOK OF CHEMISTRY AND PHYSICS, 45th edition, Robert C. Weast, editor, Chemical Rubber Company, Cleveland, Ohio (1964). The preferred Group VIII metals are iridium, ruthenium and rhodium. Zinc can be present as a promoter or co-catalytic metal in an amount within the range of about 0.1 to about 10 weight percent, expressed as the reduced metal and based upon the weight of the catalytic composition, while the Group VIII metal is present in an amount within the range of about 0.1 to about 5 weight percent, expressed as the reduced metal and based upon the weight of the catalytic composition.

It is essential that the porous refractory inorganic oxide that is employed in the catalytic composition of the present invention is a highly purified high surface area gamma or eta alumina containing essentially no silica and with a surface area of at least 100 m$^2$/g. Catalyst supports which promote hydrocracking such as silica-alumina silica-magnesia, titanium-alumina, zinc oxide-alumina, gallium oxide-alumina and the like are not suitable. Catalytically active alumina, such as gamma-alumina and eta-alumina, is the preferred refractory inorganic oxide. Such alumina should have a pore diameter of about 70 Angstroms (Å) to about 200 Angstroms (Å) and a surface area of at least 100 square meters per gram. Suitably, the surface area should be within the range of about 100 square meters per gram to about 500 square meter per gram.

The preferred support which is utilized in the process of the present invention is relatively free or substantially free from water. It is also essential that the support have a high surface area, of at least 100 m$^2$/g or more, measured by surface adsorption techniques. Gamma alumina accordingly is preferred as it has a surface area ranging from about 100 to about 300 square meters/gram. Alpha is not suitable as it has a surface area ranging from about 10 to 25 square meters per gram. In addition, aluminas which contain combined water but which have relatively high surface areas are also unsatisfactory supports. Such aluminas include dried alumina monohydrates which have not been sufficiently calcined to remove the combined or adsorbed water.

An example of the refractory inorganic oxide component that is employed in the catalyst of this invention is PHF or Aero-1000 Alumina manufactured by American Cyanamid Corp. It is described as a high-purity gamma-alumina, the typical inspection data being: surface area 206 m$^2$/g, pore volume 0.6 cc/g, average pore diameter 90 Å (Angstroms), sodium content 0.1 wt.%, silicon content 0.02 wt.%, iron content 0.025 wt.%.

While it is not desired to be bound by anything concerning the reaction mechanism of the ethyl scission process of this invention, it is theorized that the catalytic ethyl scission reaction of for example ethyltoluene is structure sensitive; that the degree of dispersion of the metal catalyst particles in the highly purified alumina support is extremely high and that accordingly the ethyl scission reaction which occurs with ethyltoluene is sensitive to the state of the dispersion of the metal per unit surface area of the support. It is theorized that the highly purified alumina containing essentially no silica is pertinent to the success of the process in that the presence of silica promotes hydrocracking and ring scission. It is also theorized that the use of the particular catalytic metal, the Group VIII metal and the Group VIII metal promoted with zinc impose the particular catalytic activity which is desired; namely the selective scission to methyl benzenes of ethyltoluene, by means of the particular surface properties imposed upon the catalyst by these metals and specific alumina support.

The catalyst composition of the present invention may be prepared in various ways. For example, the appropriate aqueous salt material in the form of a chloride solution is stirred into a sol or gel of the refractory inorganic oxide, followed by the cogelling of the sol or gel mixture by the addition of dilute ammonia. The resulting cogelled material is then dried and calcined to remove the combined or adsorbed water. As an alternate method of preparation, a hydrogel of the refractory inorganic oxide is blended with a solution or solutions of soluble compounds of the Group VIII metals. The blended mixture is then dried, pelleted, and calcined. Suitable drying conditions for use in the above described metal manufacturing methods comprise a temperature in the range of about 200° F. to about 400° F. and a drying time of about 5 to 30 hours. Suitable calcination conditions comprise a temperature in the range of about 900° to 1400° F. and a calcination time of about 2 to about 20 hours. Preferred drying and calcination conditions are a temperature of about 250° F. for about 16 hours and a temperature of about 1000° F. for about 6 hours, respectively. It is preferred that the calcination of ruthenium-containing catalysts be carried out in the absence of oxygen to avoid the formation of the volatile ruthenium tetraoxide.

The following is another method of preparation. The Group VIII salt in the form of heat-decomposable components in a finely-divided state may be added to a hydrosol or a hydrogel of the refractory inorganic oxide component and blended therein to form a homogenous mixture. These heat-decomposable components may be added in a single solution or in several solutions. The resulting composition is then thoroughly mixed, dried, and calcined, as described above.

Catalysts were tested at atmospheric pressure and at elevated pressures. The catalysts tested at atmospheric pressure were reacted in a reactor which consisted of a quartz tube, 9 inches long, having an I.D. of 0.75 inches. Heat was supplied by an electric furnace and the internal reactor temperature was measured by thermocouples located in thermowells along the reactor axis. The hydrocarbon feed was introduced by a syringe pump, and preheated to 200° C. prior to entering the catalyst bed. The reactor effluent was condensed at dry ice temperatures and the liquid product was weighed and then analyzed by gas chromatography. The catalyst testing at elevated pressures was carried out in a reactor which consisted of a stainless steel tube, 12 inches long, having an I.D. of 0.83 inches. The reactor was heated by a 3-zone electric furnace and the internal temperature was measured by a movable thermocouple located in a thermowell along the reactor axis. Hydrogen and the hydrocarbon feed were metered into the reactor through differential pressure cells. Separation of the liquid and gaseous streams was accomplished at 200 psig, and the liquid product was collected at atmospheric pressure and analyzed by gas chromatography. The gaseous products were qualitatively analyzed by an on-line gas chromotograph.

The invention comprises a process for the ethyl scission of ethylaromatics which process consists essentially of contacting an alkyl aromatic stream in a reaction zone under scission conditions and in the presence of a catalyst to furnish a product containing methyl aromatics, said catalyst comprising a metal selected from the group consisting of a Group VIII metal and a Group VIII metal promoted with zinc upon a support of a refractory inorganic oxide of highly purified alumina containing essentially no silica, having a surface area of a least 100 m$^2$/g, said alumina being selected from the group consisting of catalytically active gamma alumina or eta-alumina, and said Group VIII metal being present as a member selected from the group consisting of (1) the reduced metals, (2) the oxides, and (3) mixtures thereof.

Embodiments of the present invention may be found in the following examples. These embodiments and examples are presented for purposes of illustration only and are not intended to limit the scope of the invention.

Catalyst Preparation

Catalyst compositions were prepared with the following analyses:

| Catalyst | Analysis - Wt. Percent |
| --- | --- |
| A | 0.5% Re on $Al_2O_3$ |
| B | 0.4% Pt on $Al_2O_3$ |
| C | 0.5% Ru on $Al_2O_3$ |
| D | 0.5% Rh on $Al_2O_3$ |
| E | 0.5% Ir on $Al_2O_3$ |
| F | 0.5% Rh on $Al_2O_3$ (sulfided) |
| G | 0.5% Rh - 3.0% Zn on $Al_2O_3$ |
| H | 0.5% Ru - 3.0% Zn on $Al_2O_3$ |

The catalysts were prepared by impregnating gamma alumina with an aqueous chloride salt solution of the desired metal. Zinc was impregnated with a zinc nitrate solution. The impregnated aluminas were dried at 250° F. and then calcined at either 1000° F. in air or at 500° F. under nitrogen for 3 hours. Details of typical catalyst preparation were as follows:

0.5% Ru on $Al_2O_3$—149 g 20/40 American Cyanamid Aero 1000 alumina was impregnated with 82.4 ml of ruthenium solution (0.0091 g Ru/ml diluted to 150 ml with dist. $H_2O$). The sample was dried for about three hours at 250° F. and calcined three hours at 500° F. under nitrogen.

0.5% Rh—3.0% Zn on $Al_2O_3$—American Cyanamid Aero 1000 alumina was ground to 20/40 mesh and 145 g of this alumina was impregnated with a rhodium chloride solution containing 2 g rhodium and 20.45 g zinc nitrate dissolved in 135 ml of dist. $H_2O$. The sample was dried about three hours at 250° F. and calcined in air for three hours at 1000° F.

Catalyst loadings of 50 g were used. Before introducing the hydrocarbon feed, the catalysts were treated overnight with hydrogen at 100 cc/min. at a temperature of 800° F. in one instance with Rh/$Al_2O_3$, presulfiding was carried out with 8% $H_2S/H_2$ gas at atmospheric pressure at 500° F. The control catalyst of gamma alumina, $Al_2O_3$, was ground to 20/40 mesh, dried and calcined in air in the same procedure.

EXAMPLE I

Scission activity of catalysts A, B, C and D were evaluated relative to a control of gamma alumina using ethylbenzene as a feedstock. The process in each evaluation was carried out under hydrogen at atmospheric pressure over a 500° to 800° F. temperature range. Table I, which gives process conditions and results, illustrates the high scission activity of catalysts A, B, C and D relative to the scission activity of the control, gamma alumina, as evidenced by the high ratios of toluene to benzene.

Table I

Catalytic Dealkylation of Ethylbenzene
Effect of Temperature and Catalyst Composition on Selectivity

| Catalyst | Temp °F. | $H_2$:EB Mole Ratio | WHSV | EB Conversion wt. % | Selectivity, wt. % | | | | |
| --- | --- | --- | --- | --- | --- | --- | --- | --- | --- |
| | | | | | Toluene | Benzene | (a) | (b) | (c) |
| Control ($Al_2O_3$) | 700 | 1.2 | .03 | 2.2 | 34.5 | 37.0 | — | — | 9.6 |
| | 800 | 1.2 | .02 | 4.2 | 15.9 | 55.6 | — | — | 7.2 |
| A | 700 | 1.3 | .02 | 20.4 | 54.1 | 27.6 | — | — | 8.4 |
| (0.5% | 700 | 2.5 | .01 | 83.7 | 49.2 | 28.3 | — | .2 | 8.4 |
| Re/$Al_2O_3$) | 800 | 1.3 | .02 | 49.6 | 46.3 | 32.8 | — | — | 5.4 |
| B | 500 | 1.4 | .02 | 95.8 | — | — | 101.3 | 103.2 | — |
| (0.4% | 600 | 1.0 | .04 | 40.3 | 19.5 | 2.4 | 67.6 | 76.9 | — |
| Pt/$Al_2O_3$) | 700 | 1.0 | .11 | 27.5 | 67.3 | 13.7 | 4.2 | 5.7 | .9 |
| | 700 | 1.2 | .03 | 88.0 | 64.9 | 17.1 | .8 | 9.2 | .7 |
| | 800 | 1.2 | .04 | 80.0 | 51.1 | 25.9 | .1 | .1 | 1.8 |
| C | 500 | 1.3 | .02 | 25.2 | 48.7 | 2.1 | 33.1 | 39.1 | 4.2 |
| (0.5% | 600 | 1.0 | .06 | 22.5 | 75.2 | 7.3 | .8 | 1.4 | 7.5 |
| Ru/$Al_2O_3$) | 700 | 1.0 | .13 | 24.9 | 71.0 | 12.2 | — | — | 9.2 |
| | 700 | 1.4 | .02 | 84.1 | 67.2 | 15.7 | — | .1 | 5.5 |
| | 800 | 1.2 | .04 | 66.9 | 63.6 | 18.5 | — | — | 4.4 |
| D | 500 | 1.2 | .06 | 57.2 | 67.7 | 7.1 | 12.6 | 14.8 | 2.5 |
| (0.5% | 600 | 1.4 | .44 | 51.9 | 70.3 | 13.7 | — | — | 4.7 |
| Rh/$Al_2O_3$) | 700 | 1.2 | .63 | 36.9 | 58.7 | 23.4 | — | — | 7.5 |
| | 700 | 1.2 | .24 | 77.1 | 53.6 | 27.7 | — | — | 3.3 |
| | 800 | 1.2 | 1.0 | 37.1 | 51.4 | 29.4 | — | — | 7.1 |

(a) Ethylcyclohexane
(b) Total Saturates
(c) High Boilers
Note: Reactions were at atmospheric pressure:
Wt. % Selectivity equals Wt. Products Formed ÷ Wt. EB Reacted × 100.

EXAMPLE II

In the procedure of Example I, catalysts C, D, E and F were evaluated as to ethyl scission using ethyltoluenes as a feedstock. Process conditions and results are in Table II.

Table II

Catalytic Dealkylation of Ethyltoluene
Effect of Temperature, Pressure and Catalytic Composition on Selectivity

| Catalyst | Temp. °F. | Pressure, Atm. | H$_2$:HC Mole Ratio | WHSV | HC Conversion Mole % | X | EB | T | B | (a) | (b) | (c) |
|---|---|---|---|---|---|---|---|---|---|---|---|---|
| C | 650 | 1 | 6.0 | 0.42 | 19.1 | 72.4 | 9.4 | 14.7 | 0.9 | 2.3 | — | 0.3 |
| (0.5% Ru/Al$_2$O$_3$) | 650 | 1 | 6.1 | 0.41 | 25.1 | 69.6 | 8.6 | 15.3 | 0.7 | 2.1 | 3.5 | 0.2 |
|  | 700 | 1 | 6.1 | 0.81 | 19.0 | 65.2 | 8.8 | 16.9 | 1.0 | 2.3 | 0.1 |  |
| (d) | 700 | 14.3 | 5.1 | 0.3 | 27.2 | 67.9 | 7.4 | 12.3 | 1.9 | 2.5 | 0.5 | 7.5 |
|  | 700 | 1 | 6.2 | 0.11 | 49.1 | 59.8 | 6.6 | 28.5 | 2.9 | 2.1 | — | 0.1 |
|  | 800 | 1 | 5.9 | 1.12 | 23.7 | 58.1 | 7.9 | 25.7 | 2.5 | 1.7 | 4.1 | — |
|  | 800 | 1 | 6.2 | 0.11 | 61.9 | 44.2 | 4.4 | 41.3 | 6.9 | 1.3 | 1.8 | 0.1 |
| (d) | 800 | 14.3 | 7.8 | 0.3 | 19.1 | 61.1 | 5.5 | 18.8 | 2.6 | 5.0 | 1.9 | 5.1 |
| D | 650 | 1 | 4.9 | 1.36 | 29.5 | 64.4 | 12.6 | 15.9 | 1.5 | 1.1 | 3.6 | 0.9 |
| (0.5% Rh/Al$_2$O$_3$) | 650 | 1 | 5.2 | 0.80 | 44.6 | 58.1 | 8.8 | 26.1 | 3.0 | 1.2 | 2.7 | 0.1 |
|  | 700 | 1 | 6.4 | 1.57 | 48.2 | 55.1 | 9.9 | 30.4 | 2.9 | 1.6 | — | 0.1 |
|  | 700 | 1 | 6.2 | 0.57 | 73.9 | 49.8 | 4.6 | 38.1 | 6.5 | 0.9 | — | 0.1 |
| E | 700 | 1 | 7.1 | 0.11 | 14.5 | 67.2 | 10.6 | 19.8 | 1.3 | 0.9 | — | 0.2 |
| (0.5% Ir/Al$_2$O$_3$) | 800 | 1 | 7.2 | 0.11 | 16.0 | 55.1 | 9.9 | 30.4 | 2.9 | 1.6 | — | 0.1 |
| F | 800 | 14.3 | 5.0 | 0.11 | 30.4 | 29.4 | 4.8 | 18.2 | 2.9 | 27.9 | 2.4 | 14.4 |
| (0.5% Rh/Al$_2$O$_3$ - sulfided) |  |  |  |  |  |  |  |  |  |  |  |  |

Notes:
X - xylenes
EB - Ethylbenzenes
T - Toluene
B - Benzene
(a) - Trimethylbenzene
(b) - C$_{10}$ Aromatics
(c) - Saturates--mostly methylethylcyclohexanes
(d) - Catalyst calcined at 1000° F. in air. All other catalysts calcined at 500° F. under nitrogen.

Catalyst C, Ru/Al$_2$O$_3$, was an effective catalyst for converting ethyltoluenes to xylenes at atmospheric pressure and at 14 atmospheres. The Ru/Al$_2$O$_3$ catalyst used in the runs carried out at 14 atmospheres was calcined in air at 1000° F., whereas the catalyst used at atmospheric pressure was calcined under N$_2$ at 500° F. Selectivities to xylenes ranged between 44 and 72 mole % at ethyltoluene conversion levels of 19-62% per pass. The major by-product was toluene.

The selectivities to xylenes obtained with the Rh/Al$_2$O$_3$ catalyst at atmospheric pressure were comparable to those obtained with Ru/Al$_2$O$_3$; however, Rh/Al$_2$O$_3$ was considerably more active. When ethyltoluenes were reacted over Rh/Al$_2$O$_3$ at 14 atmospheres pressure at 700-800° F. a highly exothermic reaction was observed resulting in the formation of substantial quantities of C$_1$-C$_4$ paraffins. This was attributed to the high hydrogenation and cracking activity of Rh/Al$_2$O$_3$ at these high hydrogen pressures. Sulfiding the Rh/Al$_2$O$_3$ catalyst reduced its hydrogenation and cracking activity. However, activity and selectivity for converting ethyltoluenes to xylenes decreased relative to the unsulfided Rh/Al$_2$O$_3$ catalyst used at atmospheric pressure (Table II).

EXAMPLE III

In the procedure of Example I, catalysts G and H were evaluated as to ethyl scission using ethyltoluenes as a feedstock. Process conditions and results are in Table III.

Table III

Catalystic Dealkylation of Ethyltoluenes to Xylenes
Effect of Zinc Co-Catalyst

| Catalyst | Temp. °F. | Pressure, psig | H$_2$:HC Mole Ratio | WHSV | HC Conversion Mole % | Selectivity, Mole % | | | | | | |
|---|---|---|---|---|---|---|---|---|---|---|---|---|
|  |  |  |  |  |  | X | EB | T | B | (a) | (b) | (c) |
| G | 650 | 200 | 7.2 | 0.3 | 60.1 | 2.6 | 0.4 | — | — | — | 0.2 | 96.8 |
| (0.5% Rh - 3% Zn | 700 | 200 | 5.9 | 0.3 | 56.5 | 49.6 | 4.5 | 3.8 | — | 2.3 | 0.4 | 39.4 |
| /Al$_2$O$_3$) | 800 | 200 | 5.9 | 1.03 | 41.3 | 73.1 | 9.1 | 9.1 | 1.2 | 1.4 | 1.6 | 4.5 |
|  | 800 | 200 | 6.2 | 0.6 | 45.7 | 69.9 | 9.0 | 10.3 | 1.2 | 2.4 | 1.4 | 4.9 |
| H | 650 | 200 | 6.0 | 0.6 | 44.4 | 47.8 | 2.2 | 1.4 | — | 0.5 | 0.2 | 47.9 |
| (0.5% Ru - 3% Zn | 700 | 200 | 6.2 | 1.03 | 33.0 | 71.7 | 4.6 | 4.7 | 7.1 | 1.0 | 0.4 | 10.5 |
| /Al$_2$O$_3$) | 700 | 200 | 6.2 | 0.6 | 67.0 | 67.0 | 2.8 | 8.5 | 6.5 | 0.9 | 0.1 | 14.2 |
|  | 800 | 200 | 6.3 | 2.0 | 50.1 | 74.3 | 6.6 | 14.0 | 0.9 | 1.8 | 0.4 | 2.0 |

Table III-continued

Catalystic Dealkylation of Ethyltoluenes to Xylenes
Effect of Zinc Co-Catalyst

| Catalyst | Temp. °F. | Pressure, psig | H$_2$:HC Mole Ratio | WHSV | HC Conversion Mole % | HC Selectivity, Mole % | | | | | | |
|---|---|---|---|---|---|---|---|---|---|---|---|---|
| | | | | | | X | EB | T | B | (a) | (b) | (c) |
| | 800 | 200 | 5.7 | 1.1 | 75.0 | 66.4 | 4.0 | 23.6 | 1.6 | 1.4 | 0.2 | 2.8 |

Note:
X - Xylenes
EB - Ethylbenzenes
T - Toluene
B - Benzene
(a) - Trimethylenebenzene
(b) - C$_{10}$ Aromatics
(c) - Saturates, mostly methylcyclohexanes The addition of zinc to catalyst D, 0.5(Wt)% Rh/Al$_2$O$_3$, of Example II to form catalyst G, 0.5(Wt)%-3.0(Wt)% Zn/Al$_2$O$_3$, tempered the cracking activity of the catalyst and promoted its scission activity. This is evidenced by the 73% selectivity to xylenes obtained at a 41% conversion per pass of ethyltoluenes at 800° F. These results are in sharp contrast to the results obtained with catalyst D in Example II. However, zinc did not have a significant effect on the performance of catalyst C, 0.5(Wt)% Ru/Al$_2$O$_3$, as the xylene selectivities with catalyst C and catalyst H, 0.5(Wt)% Ru-3.0(Wt)% Zn/Al$_2$O$_3$, were comparable.

EXAMPLE IV

In the procedure of Example I, catalysts G and H were evaluated as to ethyl scission using a simulated C$_9$ fractionated heavy reformate feed stream comprising 64.4% pseudocumene and 35.6% ethyltoluenes. Pressure was 200 psig. Process conditions and results are in Table IV.

sion, as both catalysts converted the C$_9$ aromatic feed to xylenes in high selectivity. Despite the high concentration of pseudocumene in the feed, both catalysts exhibited a higher activity for converting ethyltoluenes than pseudocumene, as evidenced by the ethyltoluene/pseudocumene conversion ratios shown in Table IV.

What is claimed is:

1. A process for selective ethyl scission of ethyl aromatics to methyl aromatics which process comprises contacting an alkylaromatic feed stream comprising ethyltoluene with hydrogen in the presence of a catalyst composition comprising a metal component selected from the group consisting of a Group VIII metal and a Group VIII metal promoted with zinc, the said group VIII metal selected from the gooup consisting of ruthenium, rhodium, and iridium, upon a high surface area carrier of highly purified alumina with a surface area of at least 100 m$^2$/g. and containing essentially no silica at a temperature within the range from about 600° F. to about 1000° F., and wherein about 0.01 to about 20

Table IV

Catalytic Dealkylation of Heavy Reformate To Xylenes

| Catalyst | Temp. °F. | H$_2$:HC Mole Ratio | WHSV | HC Conversion | | | Total C$_9$ Mole % | Selectivity, Mole %$^{(a)}$ | | | | | |
|---|---|---|---|---|---|---|---|---|---|---|---|---|---|
| | | | | PS Mole % | ET Mole % | ET/PS Ratio | | X | $^{(b)}$ X/ET | $^{(c)}$ EB/T | T | B | Saturates |
| G | 700 | 5.5 | 0.3 | 17.6 | 30.2 | 1.7 | 22.1 | 13.6 | — | 8.2 | 1.4 | — | 81.0 |
| (0.5 Rh - 3 Zn | 800 | 6.0 | 1.0 | 9.7 | 23.1 | 2.4 | 14.5 | 71.7 | 50.2 | 12.9 | 6.1 | 1.2 | 13.7 |
| /Al$_2$O$_3$) | 800 | 5.7 | 0.5 | 14.0 | 35.7 | 2.6 | 21.5 | 72.5 | 52.8 | 11.9 | 7.4 | 1.3 | 11.8 |
| | 800 | 6.0 | 0.3 | 19.1 | 41.4 | 2.2 | 27.0 | 72.7 | 49.9 | 12.8 | 8.8 | 1.4 | 10.1 |
| H | 700 | 6.6 | 0.3 | 9.9 | 29.3 | 3.0 | 16.8 | 32.1 | — | 7.9 | 2.0 | 0.4 | 60.6 |
| (0.5 Ru - 3 Zn | 800 | 6.0 | 2.5 | 4.0 | 17.7 | 4.4 | 8.9 | 78.5 | 69.6 | 8.6 | 7.9 | 0.3 | 7.2 |
| /Al$_2$O$_3$) | 800 | 6.0 | 2.0 | 9.0 | 34.3 | 3.8 | 18.0 | 79.0 | 69.0 | 8.3 | 9.9 | 0.7 | 4.8 |
| | 800 | 5.7 | 0.3 | 23.0 | 65.2 | 2.8 | 38.0 | 76.4 | 61.3 | 7.2 | 13.2 | 1.0 | 5.1 |

Note:
Pressure was 200 psig
PS - Pseudocumene
ET - Ethyltoluene
X - Xylenes
T - Toluene
B - Benzene
Saturates were mostly methylethylcyclohexanes and trimethylcyclohexanes.
$^{(a)}$Normalized values determined by G.C. analysis of the liquid product and based on the total C$_9$ aromatic conversion.
$^{(b)}$Minimum selectivity to xylenes derived solely from ethyltoluenes. This assumes all of the reacted pseudocumene was converted to xylenes.
Calculated from: $\frac{\text{Total Xylene Yield} - \text{Moles Pseudocumene Reacted}}{\text{Moles Ethyltoluene Reacted}} \times 100$
$^{(c)}$Ethylbenzene selectivity is based on the ethyltoluenes that reacted.

As shown in Table IV, ring hydrogenation and cracking reactions, yielding paraffins and naphthenes, were the predominant process occurring at 700° F. As the temperature was increased to 800° F., the reaction mechanism shifted from hydrogenation to ethyl scission weights of hydrocarbon per weight of catalyst is present.

2. The process of claim 1 wherein the said Group VIII metal and the said Group VIII metal promoted with zinc is present as a member selected from the group consisting of reduced metals, the oxides and mixtures thereof.

3. The process of claim 1 wherein the said Group VIII metal comprises ruthenium being present in an amount within the range of from about 0.1 to 5 (wt) percent expressed as reduced metal and based upon the weight of the said catalyst composition.

4. The process of claim 1 wherein the said Group VIII metal comprises rhodium being present in an amount within the range of from 0.1 to about 5 (wt.) percent expressed as the reduced metal and based upon the weight of the said catalyst composition.

5. The process of claim 1 wherein the said Group VIII metal comprises iridium being present in an amount within the range of from about 0.1 to 5(wt) percent expressed as the reduced metal and based upon the weight of the said catalyst composition.

6. The process of claim 1 wherein the said metal component comprises a ruthenium/zinc component of 0.1 to 5 (wt) percent ruthenium and 0.1 to 10 (wt.) percent zinc of total weight of said catalyst composition.

7. The process of claim 1 wherein the said metal component comprises a rhodium/zinc component of 0.1 to 5.0 (wt) percent rhodium and 0.1 to 10.0 (wt.) percent zinc of total weight of said catalyst composition.

8. The process of claim 1 wherein the said alumina is gamma alumina.

9. The process of claim 1 wherein the said alkyl aromatic feed stream comprises a $C_8$–$C_{10}$ alkyl aromatic feed stream.

10. The process of claim 9 wherein the said alkyl aromatic feed stream comprises a $C_8$–$C_9$ alkyl aromatic feed stream containing trimethylbenzenes, ethyltoluenes, propylbenzenes and indan.

11. The process of claim 10 wherein the said alkyl aromatic feed stream comprises a $C_9$ alkyl aromatic feed stream comprising trimethylbenzenes, ethyltoluenes, propylbenzenes and indan.

12. The process of claim 1 wherein the reaction products are separated from unreacted feedstocks.

13. The process of claim 1 wherein the hydrogen-to-hydrocarbon mole ratio is from about 1:1 to 20:1 at pressures of from about 100 to 500 psig.

14. The process of claim 1 wherein the contact time is from 1 to 20 seconds.

15. The process of claim 1 wherein the WHSV is within the range of about 1 to about 10 weights of hydrocarbon per hour per weight of catalyst.

* * * * *

UNITED STATES PATENT OFFICE
CERTIFICATE OF CORRECTION

Patent No. 4,177,219       Dated December 4, 1979

Inventor(s) Allen I. Feinstein et al

It is certified that error appears in the above-identified patent and that said Letters Patent are hereby corrected as shown below:

| Patent Column | Line | | |
|---|---|---|---|
| 3 | 10-11 | "Hydrodealkation" should be --hydrodealkylation-- | |
| 5 | 14 | "mater" should be --meters-- | |
| 6 | 48 | "chromotograph" should be --chromatograph-- | |
| 6 | 59 | "of a least" should be --of at least-- | |
| 8 | 8 | "in one" should be ''In one-- | |
| 9 | 13 | "0.1" should be --5.0-- (Under (b) in Table II | |
| 9 | 13 | blank should be --0.1-- (Under (c) in Table II | |
| 10 | 52 | "Catalystic" should be --Catalytic-- (Heading Table) | |
| 10 | 60 | "version" should be --WHSV-- (Under Table III) | |
| 10 (Table III) | 60 | "HC Con- Selec- tivity, Mole % Mole %  should be | --HC Conversion Mole %-- |

UNITED STATES PATENT OFFICE
CERTIFICATE OF CORRECTION

Patent No. 4,177,219　　　　　Dated December 4, 1979

Inventor(s) Allen I. Feinstein et al

It is certified that error appears in the above-identified patent and that said Letters Patent are hereby corrected as shown below:

| Patent Column | Line | |
|---|---|---|
| 10 | 60 | blank should be --Selectivity, Mole %-- (over last 7 columns, Table III) |
| 11 | | errors in "Table III - continued" headings same as in Table III |
| 11 | 15 | "(a) Trimethylenebenzene" should be --(a) Trimethylbenzene-- |
| 11 | 20 | "0.5(Wt)%-3.0(Wt)% $Zn/Al_2O_3$" should be --0.5(Wt)% Rh-3.0(Wt)% $Zn/Al_2O_3$-- |
| 12 | 33 | "gooup" should be --group-- |

Signed and Sealed this

Thirtieth Day of September 1980

[SEAL]

Attest:

SIDNEY A. DIAMOND

Attesting Officer　　　Commissioner of Patents and Trademarks